(12) United States Patent
Lappe et al.

(10) Patent No.: US 7,196,128 B2
(45) Date of Patent: Mar. 27, 2007

(54) CARBOXYLIC ESTERS BASED ON LIMONENE ALCOHOL [3-(4'-METHYLCYCLOHEXYL)BUTANOL] AND HAVING A LOW MELTING POINT

(75) Inventors: Peter Lappe, Dinslaken (DE); Christoph Balzarek, Duisburg (DE)

(73) Assignee: Celanese Chemicals Europe GmbH (DE)

( * ) Notice: Subject to any disclaimer, the term of this patent is extended or adjusted under 35 U.S.C. 154(b) by 343 days.

(21) Appl. No.: 10/886,967

(22) Filed: Jul. 8, 2004

(65) Prior Publication Data

US 2005/0065254 A1    Mar. 24, 2005

(30) Foreign Application Priority Data

Sep. 20, 2003   (DE)   ................. 103 43 623

(51) Int. Cl.
*C07C 69/66* (2006.01)
*C08K 5/09* (2006.01)
(52) U.S. Cl. .................. 524/306; 560/188
(58) Field of Classification Search ........ 524/306; 560/188
See application file for complete search history.

(56) References Cited

U.S. PATENT DOCUMENTS 2,889,354 A    6/1959    Blake et al.

FOREIGN PATENT DOCUMENTS

GB    880 961    10/1961

*Primary Examiner*—Taylor Victor Oh
(74) *Attorney, Agent, or Firm*—Charles A. Muserlian

(57) ABSTRACT

A carboxylic ester of the formula

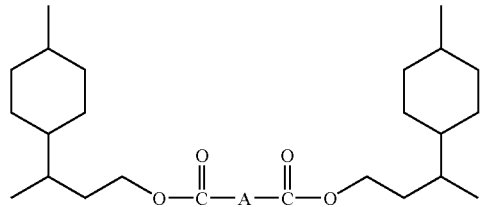

in which A is —$(CH_2)_x$— where x=1–10, a process for its preparation which esters are useful lubricated and plasticizers for high molecular polymeric thermoplastics.

5 Claims, No Drawings

CARBOXYLIC ESTERS BASED ON LIMONENE ALCOHOL [3-(4'-METHYLCYCLOHEXYL)BUTANOL] AND HAVING A LOW MELTING POINT

The present invention relates to novel carboxylic esters based on limonene alcohol, to processes for their preparation and to their use.

STATE OF THE ART

Carboxylic esters find use in industry to a great extend and in various ways, for example as lubricants, plasticizers and ordorants. In industry, numerous different esters are used, starting from simple carboxylic esters composed of monocarboxylic acids and monoalcohols up to complex ester oils composed of mixtures of mono- and dicarboxylic acids with mono- and polyfunctional alcohols. The selection of suitable starting products allows the physical properties, for example boiling point of viscosity, to be precisely adjusted, and the chemical properties, for example the hydrolysis stability or the stability toward oxidative degradation, to be taken into account. It is also possible to selectively tailor carboxylic esters precisely to the solution of specific application problems.

Comprehensive reviews of the use of carboxylic esters can be found, for example, in Ullmann's Encyclopedia of Industrial Chemistry, $5^{th}$ Edition, 1988, VCH; Vol. A11, pages 191–193, Vol. A15, pages 438–440, Vol. A20, pages 439–458; Synthetic Lubricants and High-Performance Functional Fluids, Marcel Dekker Inc., 1999, $2^{nd}$ Edition, pages 63–102; Common Fragrance and Flavor Materials, Wiley-VCH 2001.

The use of carboxylic esters as lubricants is of great industrial significance. Strictly speaking, the term "lubricants" includes only products which are used for the lubrication of sliding or rolling elements. The lubricants used in numerous applications in industry consist predominantly of mineral oils or fully or partly synthetic products. Lubricants based on mineral oils can be used in various ways. They not only serve for lubrication and power transfer at high and low temperatures, but also for heat transfer and insulation. For requirements which are fulfilled only incompletely by mineral oil products, synthetic liquids having lubricant oil-like character may lead to technically better solutions. Synthetic base oils are prepared from substantially uniform substances under controlled conditions and may belong to various chemical compound classes.

A particularly important compound class is that of the ester oils. They are used to a great extend, for example, in aviation as turbine engine and instrument oils, as greases or gun oils. These ester oils are prepared by the reaction of acids or acid anhydrides, especially of mono- or dicarboxylic acids and alcohols, especially of mono, di-, tri- or tetraalcohols.

Industrially important starting materials for esters are, for example, aliphatic monocarboxylic acids having 5–10 carbon atoms. Dicarboxylic acids available in industrial amounts are adipic acid, azelaic acid or sebacic acid. In addition to the aliphatic alcohols such as 2-ethylhexanol, useful alcohols are in particular polyhydric alcohols such as ethylene glycol and its oligomers, di-, tri- and tetraethylene glycol, propylene glycol and its oligomers, 1,3-propanediol, 1,4-butanediol, 1,6-hexanediol, neopentyl glycol, trimethylolpropane, glycerol and pentaerythritol.

The development of modem lubricants and their correct application are of considerable economic importance. Lubricants matched optimally to the particular task provide considerable savings by saving energy, reducing wear, reducing maintenance times and increasing overhaul intervals. Despite the numerous products introduced in everyday life and in industry, there is therefore still a need for novel lubricants having improved properties. The viscosity and solidification point behavior in particular of esters compounds is a critical property at low temperatures for many applications. The kinematic viscosity values are determined to DIN 51562/ASTM D445. The cold performance of esters is described by its solidification point or the pour point. It is generally measured to ASTM D97.

The use of carboxylic esters as plasticizers is likewise of great economic significance. Plasticizers find use to a great extent and in various ways in plastics, coatings, sealants and rubber-like articles. They interact physically, without reacting chemically, with high molecular weight, polymeric thermoplastics, preferably by their dissolution and swelling capacity. This forms a homogeneous system whose thermoplastic range has been shifted to lower temperatures compared to the original polymers, with results including optimization of the mechanical properties, for example, reshaping capacity, elasticity, strength are increased and the hardness is reduced. In order to open up as many fields of application as possible for plasticizers, they have to fulfill a series of criteria. Ideally, they should be odorless, colorless, and light-, cold- and heat-resistant. Moreover, it is expected that they are insensitive toward water, have low flammability and low volatility and do not damage health. In addition, the preparation of the plasticizers should be simple and, in order to satisfy ecological requirements, proceed with avoidance of waste substances such as unutilizable by-products and wastewaters comprising harmful substances.

The most important plasticizers include the esters of di- and polycarboxylic acids with plasticizer alcohols, i.e. unbranched or branched primary alcohols having from about 6 to 20 carbon atoms, which are used as individual compounds or else as mixtures. High-volume ester plasticizers used are in particular phthalic esters for plasticizing PVC.

A special class of ester plasticizers which are also abbreviated by the "G-ester" designation comprises, as the alcohol component, diols or ether diols, specifically ethylene glycol, diethylene glycol, triethylene glycol and tetraethylene glycol.

As also in the case of lubricants, the development of modem plasticizers which are tailored to the particular performance objective is of considerable economic significance. The demand for plasticizers matched optimally to the particular task and having improved properties is of great interest despite the numerous products introduced on the market.

Aside from the efforts to precisely adjust the performance properties of ester compounds, efforts have been made for some time to obtain the starting materials of ester compounds, i.e. the acid and/or the alcohol component, from renewable raw materials, and thus to give greater weight to this raw material basis compared to the crude oil basis. Examples of such ester compounds and their use as lubricants are the neopentyl, trimethylolpropane or pentaerythritol esters based on oleic acids, for example the products Edenor® PDO or Edenor® 2742 from Cognis.

OBJECTS OF THE INVENTION

It is therefore an object of the invention to provide novel carboxylic esters which can be used with particularly good success as lubricants or plasticizers, and which are based on renewable raw materials.

It is likewise an object of the invention to provide a process which allows such carboxylic esters to be prepared from readily available starting materials, available inexpensively in a sufficient amount and based on renewable raw materials and particular value is placed on the esterification process being realizable by simple technical means and not requiring any complicated or specialized apparatus.

The invention will become obvious from the following detailed description.

THE INVENTION

The invention relates to novel carboxylic esters of the formula

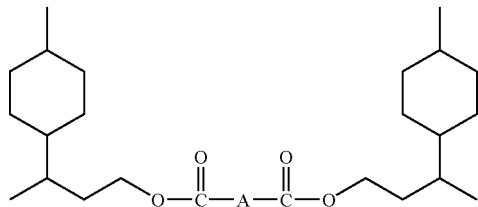

wherein A is $-(CH_2)_x-$ where x=1–10.

The alcohol component used in the novel ester compounds is limonene alcohol [3-(4'-methylcyclohexyl)butanol]. Limonane alcohol is prepared as the alcohol component by hydroformylating limonene which is available inexpensively in large amounts and is obtained from ethereal oils, for example, from orange oil or pineneedle oil. Limonene finds use for perfuming laundry detergents, and also in the dyes and coatings industry.

The hydroformylation, carried out under Rh catalysis, of limonene leads in very high yields to limonene aldehyde [3-(4'-methyl-3-cyclohexen-1-yl)-butyraldehyde]. The reaction with synthesis gas is generally effected in a customary organic solvent such as cyclohexane, toluene or n-hexane, at temperatures of 80° to 150° C. and pressures of 10 to 30 MPa, in the presence of known organic phosphorus (III) compounds, for example, triphenylphosphine, as ligands.

Limonene aldehyde is obtained from the crude hydroformylation product by distillative workup and is subsequently reacted in the presence of customary hydrogenation catalysts with hydrogen at elevated pressure and elevated temperature to give limonene alcohol. It is possible to use hydrogenation catalysts common in industry, for example, supported or unsupported metal catalysts which comprise, for example, nickel, palladium or copper as the catalytically active metal. In addition, promoters such as zirconium or manganese may optionally be present. Customary support materials are silicon dioxide or aluminum oxide.

The hydrogenation reaction is carried out under customary temperature conditions in a range from 70 to 150° C. and common pressure conditions in a range from 2 to 30 MPa. The hydrogenation reaction proceeds in high yields whereby limonene alcohol is thus available inexpensively in a technically simple process for the preparation of novel carboxylic esters.

The dicarboxylic acids used are in particular the aliphatic representatives, malonic acid (x=1), succinic acid (x=2), glutaric acid (x=3), adipic acid (x=4), azelaic acid (x=7), sebacid acid (x=8) and 1,12-dodecanedioic acid (x=10). These simple representatives of the aliphatic dicarboxylic acids are available on the industrial scale or can be prepared by known processes.

The direct esterification of alcohols with carboxylic acids is one of the basic operations of organic chemistry. To increase the reaction rate, the reaction is typically carried out in the presence of catalysts. The use of one of the reactants in excess and/or the removal of the water formed in the course of the reaction ensures that the equilibrium is shifted, in accordance with the law of mass action, to the side of the reaction product, that is of the ester, i.e. high yields are achieved.

For the removal of the water of reaction formed in the ester formation, various processes are known. Preferably finding use are azeotropic distillation in the presence of a water-immiscible solvent, the heating of the reaction mixture while passing through an inert gas, the reaction of the alcohol and carboxylic acid starting materials under reduced pressure or in the presence of a desiccant.

The removal of water by azeotropic distillation has been found to be especially useful for the establishment of the equilibrium in the preparation of esters. Typically used as the azeotroping agents are organic solvents which are available inexpensively on the industrial scale. However, also suitable are all other organic substances having an appropriate boiling point which form azeotropes with water. Examples of azeotroping agents used are hexane, 1-hexane, cyclohexane, toluene, benzene.

The amount of azetroping agent required to fully remove the water can be calculated in a simple manner from the formation of water calculated in accordance with the stoichiometry of the esterification reaction and from the composition of the binary azeotrope. It has been found to be useful to use the azeotroping agent in excess, appropriately in a proportion which is from 50 to 200% by weight above the theoreticalloy calculated amount. Collection and separation of the azeotroping agent/water mixture which has been distilled off can be used in a simple manner to monitor the progress of the reaction. The azeotroping agent separated from the azeotrope may be recycled directly into the reaction, i.e. without the intermediate insertion of a purification stage.

The reaction of limonene alcohol and carboxylic acid may be carried out without using a catalyst. This variant of the reaction has the advantage that addition of extraneous substances, which can lead to undesired contamination of the ester, is prevented. However, it is then generally necessary to maintain higher reaction temperatures, because only thus is it ensured that the reaction commences with an adequate, i.e. economically acceptable rate. In this context, it has to be taken into account that the increase in the reaction temperature can lead to thermal damage to the ester. It is therefore not always possible to avoid the use of a catalyst, which eases the reaction and increases the reaction rate.

Frequently, the catalyst may be an excess of the acid which is simultaneously a reaction component of limonene alcohol. Otherwise, the customary esterification catalysts are suitable for influencing the reaction rate, such as mineral acids such as sulfuric acid, phosphoric acid, polyphosphoric acid or its acidic salts, trialkyl or triaryl phosphates, formic acid, methanesulfonic acid or p-toluenesulfonic acid.

The amount of catalyst used may extend over a wide range and it is possible to use from 1 to 10 mol % of catalyst, based on dicarboxylic acids used. However, since larger amounts of catalyst hardly result in any advantages, the catalyst concentration is typically from 2 to 8 mol %, preferably from 3 to 6 mol %, based in each case on the dicarboxylic acid used. Appropriately, a decision is made in each individual case, optionally by preliminary experiments, as to whether operation should be effected without catalyst at higher temperature or with catalyst at lower temperature.

The esterification may be undertaken in stoichiometric amounts of limonene alcohol and acid. However, preference is given to using limonene alcohol in excess in order to achieve substantially complete conversion in a finite time.

The reaction between limonene alcohol and the acid sets in, depending on the starting materials, in the range from about 80° to 110° C. and it may be conducted to completion at atmospheric pressure at temperatures of 160° to 200° C. These temperature data are guidelines which are appropriately complied with. Lower temperatures may suffice, for example, when, in a specific case, an adequately high reaction rate is achieved or only partial conversions are desired. Higher temperatures are possible when the occurrence of decomposition products which have the effects including discooration can be ruled out. The application of reduced or elevated pressure is not ruled out, but is restricted to special cases.

The reaction mixture obtained on completion of conversion comprises, in addition to the ester as the desired reaction product, in some cases unconverted starting materials, especially excess limonene alcohol when operation has been effected with an alcohol excess. For workup, the reactor effluent is freed of catalyst by conventional processes. When the catalyst is present as a solid, for example in the form of a hydrogen sulfate, the product is filtered in customary filter apparatus at a standard temperature or at temperatures of up to 150° C. The filtration may be promoted by common filtration assistants such as alumina, silica gel, kieselguhr, activated carbon. Subsequently, excess and unconverted starting materials are distilled off.

To remove last residues of acidic constituents, it is also possible to provide a treatment with an alkaline reagent, for example aqueous sodium carbonate or sodium hydroxide solution. After phase separation, the ester is dried, for example, by passing an inert gas through the product or applying vacuum. When the catalyst is dissolved in the reaction mixture, such as sulfuric acid or para-toluene sulfonic acid, starting materials still present, optionally after preceding filtration, are initially distilled off followed by treatment with an alkaline reagent. Optionally, the product is subjected to a steam distillation before the actual drying step.

If required by the intended use, the isolation of the ester may be followed by further purification steps, for example a fractional distillation under reduced pressure.

The esterification reaction may be carried out batchwise or else continuously in the reaction apparatus typical for chemical technology. It has been found that stirred tanks which are equipped with heating apparatus and a device for feeding the azeotroping agent are useful.

Owing to their outstanding viscosity and cold performance, the inventive ester compounds have excellent suitability as lubricants which are used at low temperatures but which nevertheless have a high molecular weight. In addition, the inventive esters are readily obtainable from the renewable raw material limonene. They are likewise suitable as plasticizers for many common high molecular weight polymeric thermoplastics.

The examples which follow serve to illustrate the invention without restricting it thereto.

EXAMPLE 1

Preparation of di(3-(4'-methylcyclohexyl)butyl)malonate 72.8 g of malonic acid (0.7 mol), 279.3 g (1.6 mol) of 3-(4'-methylcyclohexyl)butanol, 6.6 g of p-toluene sulfonic acid monohydrate (0.035 mol) and 50 g of toluene were initially charged in a 1 three neck flask equipped with stirrer, internal thermometer and water separator and healed to reflux. Within 60 minutes, 26.2 g of water were separated and the temperature of the reaction mixture increased toward the end of the reaction to 176° C. the reaction mixture was cooled to room temperature and admixed with 18.6 g of aqueous hydroxide (1% by weight) and 64.3 g of water. After phase separation, the organic phase was washed twice with a total of 227.2 g of water. After separating the phases twice, the organic phase (394.5 g) was fractionally distilled at a top temperature of 208° C. and a pressure of 100 Pa temperature. The ester (221.8 g) was isolated in a purity of 92.6% and corresponded to a yield of 77.1% of theory.

EXAMPLE 2

Preparation of di(3-(4'-methylcyclohexyl)butyl)succinate 82.7 g of succinic acid (0.7 mol), 279.3 g (1.6 mol.) of 3-(4'-methylcyclohexyl)butanol, 6.6 g of p-toluene sulfonic acid monohydrate (0.035 mol) and 50 g of toluene were initially charged in a 1 three-neck flask equipped with stirrer, internal thermometer and water separator and were heated to reflux. Within 60 minutes, 26.8 g of water were separated out and the temperature of the reaction mixture increased toward the end of the reaction to 178° C. The reaction mixture was cooled to room temperature and was admixed with 15.8 g of aqueous sodium hydroxide (1% by weight) and 85.3 g of water. After phase separation, the organic phase was washed twice with a total of 224.4 g of water. After separating the phases twice, the organic phase (430.5) was fractionally distilled at a top temperature of 205° C. and a pressure of 100 Pa temperature. The ester (252.0 g) was isolated in a purity of 91.0% which corresponded to a yield of 85.7% of theory.

EXAMPLE 3

Preparation of di(3-(4'-methylcyclohexyl)butyl)glutarate 92.5 g of glutaric acid (0.7 mol), 279.3 g (1.6 mol) of 3-(4'-methylcyclohexyl)butanol, 6.6 g of p-toluene sulfonic acid monohydrate (0.035 mol) and 50 g of toluene were initially charged in a 1 three-neck flask equipped with stirrer, internal thermometer and water separator and were heated to reflux. Within 60 minutes, 26.5 g of water were separated out and the temperature of the reaction mixture increased toward the end of the reaction to 176° C. The reaction mixture was cooled to room temperature and admixed with 11.0 g of aqueous sodium hydroxide (1% by weight) and 84.1 g of water. After phase separation, the organic phase was washed twice with a total of 268.4 g of water. After separating the phases twice, the organic phase (384.5 g) was fractionally distilled at a top temperature of 207° C. and a pressure of 100 Pa temperature. The ester (244.0 g) was isolated I a purity of 99.9% which corresponded to a yield of 80.0% of theory.

EXAMPLE 4

Preparation of di(3-(4'-methylcyclohexylz)butyl Adipate 102.3 g of adipic acid (0.7 mol), 279.3 (1.6 mol) of 3-(4-methylcyclohexyl)butanol, 6.6 g of p-touene sulfonic acid monohydrate (0.035 mol) and 50 g of toluene were initially charged in a 1 three-neck flask equipped with stirrer, internal thermometer and water separator and were heated to reflux. Within 60 minutes, 27.2 g of water were separated out and the temperature of the reaction mixture increased toward the end of the reaction to 184° C. The reaction mixture was cooled to room temperature and admixed with 16.1 g of aqueous sodium hydroxide (1% by weight) and 106.4 g of water. After phase separation, the organic phase was washed twice with a total of 245.3 g of water. After separating the phases twice, the organic phase (410.5 g) was fractionally distilled at a top temperature of 210° C. and a pressure of 100 Pa temperature. The ester (290.0 g) was isolated in a purity of 91.7% which corresponded to a yield of 91.4% of theory.

EXAMPLE 5

Preparation of di(3-(4'-methylcyclohexyl)butyl)sebacate 161.8 g of sebacic acid (0.8 mol), 290.2 g (1.6 mol) of 3-(4'-methylcyclohexyl)butanol, 7.6 g of p-toluenesulfonic acid monohydrate (0.040 mol) and 50 g of toluene were initially charged in a 1 three-neck flask equipped with stirrer, internal thermometer and water separator and were heated to reflux. Within 60 minutes, 30.2 g of water were separated out and the temperature of the reaction mixture increased toward the end of the reaction to 186° C. The reaction mixture was cooled to room temperature and admixed with 162.2 g of aqueous sodium hydroxide (1% by weight). After phase separation, the organic phase was washed twice with a total of 911.9 g of water. After separating the phases twice, the organic phase (435.9 g) was freed of low boilers at a bottom temperature of 240° C. and a pressure of 100 Pa. After temperature distillation on a thin-film evaporator at a jacket temperature of 240° C. and a pressure of 100 Pa, the ester (321.8 g) was isolated in a plurality of 95.6% which corresponded to a yield of 79% of theory.

TABLE

Properties of the ester compounds

| Ester | $V_{40}$ mm$^2$/s | $V_{100}$ mm$^2$/s | Pour Point ° C. |
|---|---|---|---|
| Di(3-4'-methylcyclohexyl)butyl) malonate | 30.9 | 4.9 | −51 |
| Di(3-4'-methylcyclohexyl)butyl) succinate | 41.1 | 5.8 | −42 |
| Di(3-4'-methylcyclohexyl)butyl) glutarate | 38.4 | 5.9 | −54 |

TABLE-continued

Properties of the ester compounds

| Ester | $V_{40}$ mm$^2$/s | $V_{100}$ mm$^2$/s | Pour Point ° C. |
|---|---|---|---|
| Di(3-4'-methylcyclohexyl)butyl) adipate | 38.5 | 6.0 | ≦−45 |
| Di(3-4'-methylcyclohexyl)butyl) sebacate | 50.2 | 7.7 | ≦−48 |

Determination of the kinematic viscosity to DIN 51562/ASTM D445.

Determination of the pour point to ASTM D07.

Based on the renewable raw material limonene, it is possible via the readily accessible immediate limonene alcohol to obtain dicarboxylic esters which, despite a higher molecular weight, feature outstanding viscosity and cold properties.

Various modifications of the products and process of the invention may be made without departing from the spirit or scope thereof. It is to be understood that the invention is intended to be limited only as defined in the appended claims.

What is claimed is:

1. A carboxylic ester of the formula

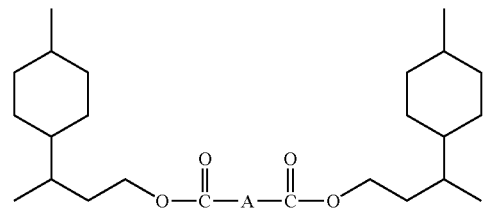

in which A is —(CH$_2$)$_x$— where x=1–10.

2. A carboxylic ester as claimed in claim 1, wherein x is 1, 2, 3, 4, 7, 8 or 10.

3. A process for preparing a carboxylic ester as claimed in claim 1, by reacting 3,4'-(methylcycloexyl)butanol with dicarboxylic acids of the formula

or their anhydrides of the formula

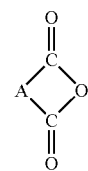

where A is as defined in claim 1, in the presence of an azeotroping agent to remove the water formed in the course of the reaction as an azeotropic mixture, and optionally in the presence of a catalyst selected from the group consisting of sulfuric acid, phosphoric acid, polyphosphoric acid or its acidic salts, trialkyl or triaryl phosphates, formic acid, methanesulfonic acid and p-toluenesulfonic acid, removing excess and unreacted starting materials, treating the product with an alkaline reagent to remove acidic constituents, optionally subsequent steam distillation, and finally drying or fractional distillation.

4. In a high molecular weight polymeric thermoplastic, the improvement comprising containing an ester of claim 1 as a lubricant.

5. In a high molecular weight polymeric thermoplastic, the improvement comprising containing an ester of claim 1 as a plasticizer.

* * * * *